United States Patent
Higuchi (10) Patent No.: US 8,896,727 B2
(45) Date of Patent: Nov. 25, 2014

(54) IMAGE PROCESSING APPARATUS, METHOD, AND COMPUTER-READABLE RECORDING MEDIUM HAVING IMAGE PROCESSING PROGRAM RECORDED THEREON

(75) Inventor: Keiji Higuchi, Tokyo (JP)

(73) Assignee: Olympus Corporation, Tokyo (JP)

( * ) Notice: Subject to any disclaimer, the term of this patent is extended or adjusted under 35 U.S.C. 154(b) by 626 days.

(21) Appl. No.: 13/207,699

(22) Filed: Aug. 11, 2011

(65) Prior Publication Data

US 2012/0033108 A1 Feb. 9, 2012

Related U.S. Application Data

(63) Continuation of application No. PCT/JP2010/052297, filed on Feb. 17, 2010.

(30) Foreign Application Priority Data

Feb. 18, 2009 (JP) ................................. 2009-035597

(51) Int. Cl.
  *H04N 5/217* (2011.01)
  *H04N 5/232* (2006.01)
  *G06T 5/00* (2006.01)
  *A61B 1/04* (2006.01)

(52) U.S. Cl.
  CPC ................ *H04N 5/217* (2013.01); *H04N 5/232* (2013.01); *G06T 5/002* (2013.01); *A61B 1/04* (2013.01); *G06T 2207/20012* (2013.01); *H04N 5/23245* (2013.01)
  USPC .......................... 348/241; 348/222.1; 382/312

(58) Field of Classification Search
  USPC ............. 348/222.1, 241, 229.1; 382/312, 266
  See application file for complete search history.

(56) References Cited

U.S. PATENT DOCUMENTS

| 8,019,174 | B2 | 9/2011 | Tsuruoka |
| 2004/0201757 | A1 | 10/2004 | Okada |
| 2005/0099515 | A1* | 5/2005 | Tsuruoka ...................... 348/241 |
| 2007/0086674 | A1 | 4/2007 | Guan |

(Continued)

FOREIGN PATENT DOCUMENTS

| CN | 101282417 A | 10/2008 |
| CN | 101283603 A | 10/2008 |

(Continued)

OTHER PUBLICATIONS

Chinese Office Action dated Jun. 7, 2013 in counterpart Chinese Application No. 2201080007972.3.

(Continued)

*Primary Examiner* — Tuan Ho
(74) *Attorney, Agent, or Firm* — Holtz, Holtz, Goodman & Chick PC (57) ABSTRACT

An object is to improve noise reduction. Provided are an image-capturing-mode selecting portion (104) that selects one image-capturing mode from a plurality of image-capturing modes; and a noise-reduction processing portion (110) that performs noise-reduction processing for input image signals by employing, in the case in which the image-capturing mode selected by the image-capturing-mode selecting portion (104) is a specific image-capturing mode, an applied noise model in which a noise model employed for a predetermined signal-value region differs from a reference noise model determined on the basis of properties of an image-acquisition element.

3 Claims, 7 Drawing Sheets

(56) References Cited

U.S. PATENT DOCUMENTS

| | | |
|---|---|---|
| 2007/0132864 A1 | 6/2007 | Tsuruoka |
| 2007/0206885 A1 | 9/2007 | Wen |
| 2008/0158395 A1 | 7/2008 | Tsuruoka |
| 2008/0204577 A1 | 8/2008 | Tsuruoka |
| 2008/0239094 A1 | 10/2008 | Baqai et al. |
| 2008/0273793 A1* | 11/2008 | Oishi ............................ 382/167 |
| 2009/0066787 A1 | 3/2009 | Yamazaki |
| 2009/0115921 A1 | 5/2009 | Fujinoki et al. |
| 2009/0167901 A1 | 7/2009 | Aragaki |

FOREIGN PATENT DOCUMENTS

| | | |
|---|---|---|
| EP | 1 764 738 | 3/2007 |
| EP | 1 931 134 A1 | 6/2008 |
| EP | 1 947 840 | 7/2008 |
| EP | 2 016 884 A1 | 1/2009 |
| JP | 06-190179 A | 7/1994 |
| JP | 11-298847 A | 10/1999 |
| JP | 2004-304526 A | 10/2004 |
| JP | 2005-303802 A | 10/2005 |
| JP | 2006-279162 A | 10/2006 |
| JP | 2006-308891 A | 11/2006 |
| JP | 2008-085975 A | 4/2008 |
| WO | WO 2007/111114 A1 | 10/2007 |

OTHER PUBLICATIONS

Extended European Search Report (EESR) dated Dec. 3, 2012 (in English) issued in counterpart European Application No. 10743751.9.

* cited by examiner

FIG. 10

IMAGE PROCESSING APPARATUS, METHOD, AND COMPUTER-READABLE RECORDING MEDIUM HAVING IMAGE PROCESSING PROGRAM RECORDED THEREON

CROSS-REFERENCE TO RELATED APPLICATIONS

This is a continuation of International Application PCT/JP2010/052297, with an international filing date of Feb. 17, 2010, which is hereby incorporated by reference herein in its entirety.

TECHNICAL FIELD

The present invention relates to an image processing apparatus, an image processing method, and an image processing program that are suitable for performing noise reduction of input image signals.

BACKGROUND ART

In the related art, as a method of reducing noise in video signals, a method has been proposed in which generated noise levels are modeled, noise levels generated in input video signals are estimated on the basis of the noise model, and then noise reduction processing is performed. For example, in Patent Literature 1, a method is proposed in which a noise level is calculated on the basis of input video signals and a reference noise model.

CITATION LIST

Patent Literature

{PTL 1} Japanese Unexamined Patent Application, Publication No. 2005-303802.

SUMMARY OF INVENTION

Technical Problem

However, with the method disclosed in the above-described Patent Literature 1, there is a problem in that noise in dark parts is hardly reduced for the following reasons.

For example, in the case of noise reduction employing the reference noise model, the amount of noise corresponding to an image acquisition element increases with increasing brightness of input video signals. Therefore, if noise reduction is performed by employing the reference noise model, it is determined that a noise level is high in bright portions and the noise reduction effect thereof is improved; however, noise reduction is not very effective in dark parts.

The present invention has been conceived in order to solve the above-described problems, and an object thereof is to provide an image processing apparatus, an image processing method, and an image processing program that are capable of creating a difference in noise reduction between a predetermined signal-value region, such as a dark part, etc., and other regions.

Solution to Problem

A first aspect of the present invention is an image processing apparatus including image-capturing-mode selecting portion configured to select one image-capturing mode from a plurality of image-capturing modes; and noise-reduction processing portion configured to perform noise reduction processing on input image signals by employing, in the case in which an image-capturing mode selected by the image-capturing-mode selecting portion is a specific image-capturing mode, an applied noise model in which a noise model for a predetermined signal-value region differs from a reference noise model determined on the basis of properties of an image-acquisition element.

A second aspect of the present invention is a computer-readable recording medium having recorded thereon an image processing program for causing a computer to execute, image-capturing-mode selecting processing for selecting one image-capturing mode from a plurality of image-capturing modes; and noise-reduction processing for performing noise reduction processing on input image signals by employing, in the case in which the selected image-capturing mode is a specific image-capturing mode, an applied noise model in which a noise model for a predetermined signal-value region differs from a reference noise model determined on the basis of properties of an image-acquisition element.

A third aspect of the present invention is an image processing method including a step of selecting one image-capturing mode from a plurality of image-capturing modes; and a step of performing noise reduction processing on input image signals by employing, in the case in which the selected image-capturing mode is a specific image-capturing mode, an applied noise model in which a noise model for a predetermined signal-value region differs from a reference noise model determined on the basis of properties of an image-acquisition element.

Advantageous Effects of Invention

The present invention affords an advantage in that noise reduction in a dark part can be improved.

DESCRIPTION OF EMBODIMENTS

Embodiments of an image processing apparatus according to the present invention will be described below in detail with reference to the drawings.

First Embodiment

Figure 1:
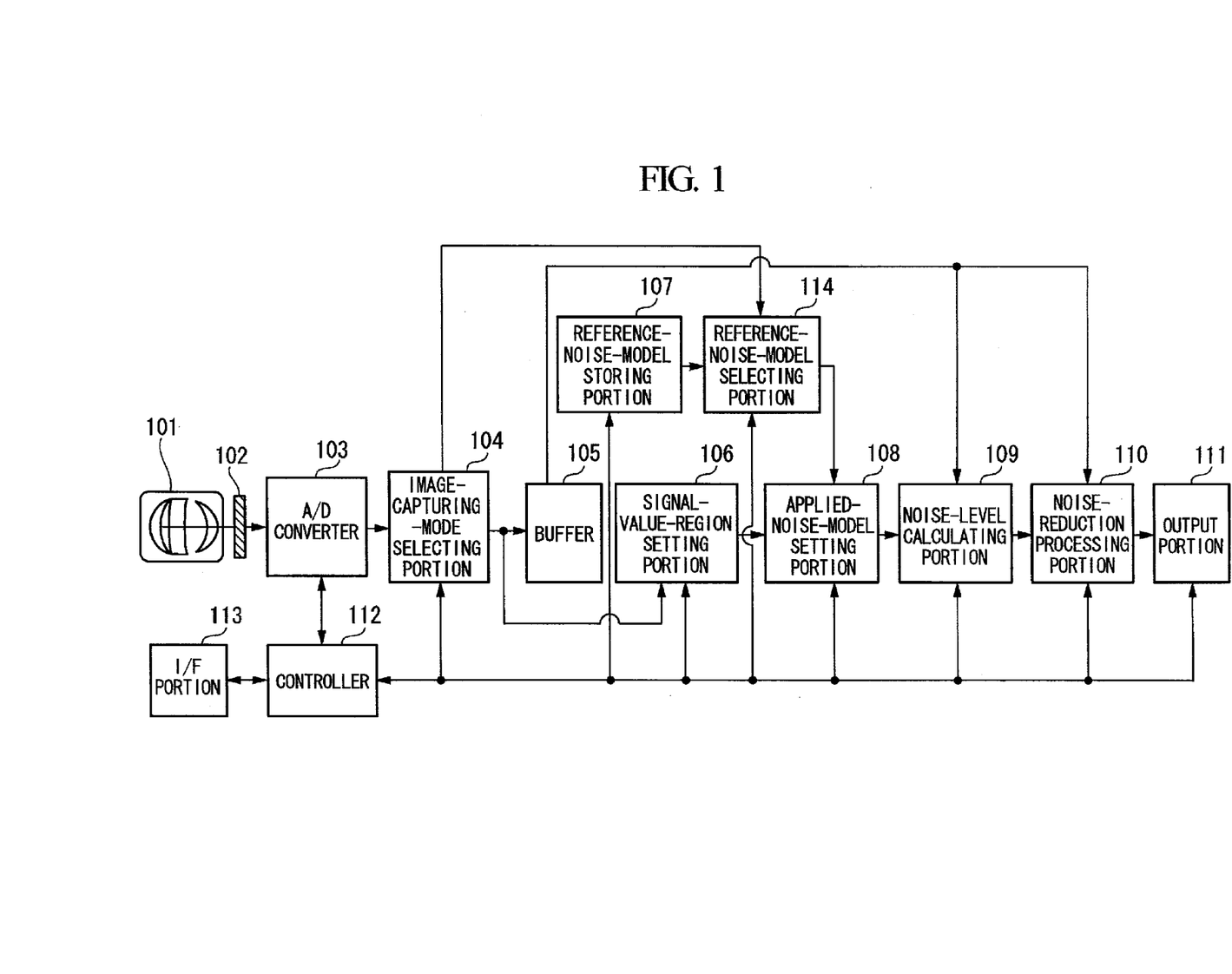
FIG. 1 is a diagram showing an example configuration of an image processing apparatus according to first and second embodiments of the present invention.

FIG. 1 is a block diagram showing an example configuration of an image acquisition system according to a first embodiment of the present invention. The image acquisition system according to this embodiment is, for example, a digital camera and is provided with an image acquisition apparatus, which includes a lens system 101 and a CCD 102, and an image processing apparatus that applies various kinds of image processing, such as noise-reduction processing, etc., to image signals acquired by the image acquisition apparatus.

In the image processing apparatus of the image acquisition system, an A/D converter 103 is connected to an image-capturing-mode selecting portion 104. The image-capturing-mode selecting portion 104 is connected to a buffer 105 and a signal-value-region setting portion 106. The buffer 105 is connected to a noise-level calculating portion 109 and a noise-reduction processing portion 110. The signal-value-region setting portion 106 is connected to an applied-noise-model setting portion 108. A reference-noise-model storing portion 107 is connected to a reference-noise-model selecting portion 114. The reference-noise-model selecting portion 114 is connected to an applied-noise-model setting portion 108. The applied-noise-model setting portion 108 is connected to the noise-level calculating portion 109. The noise-level calculating portion 109 is connected to the noise-reduction processing portion 110. The noise-reduction processing portion 110 is connected to an output portion 111.

In addition, a controller 112, such as a microcomputer, is bidirectionally connected to the A/D converter 103, the image-capturing-mode selecting portion 104, the signal-value-region setting portion 106, the reference-noise-model storing portion 107, the applied-noise-model setting portion 108, the noise-level calculating portion 109, the noise-reduction processing portion 110, and the output portion 111. In addition, an external interface (hereinafter, abbreviated as I/F) portion 113 provided with a power switch and an interface for setting variables is also bidirectionally connected to the controller 112.

The A/D converter 103 converts analog image signals input via the lens system 101 and the CCD (image acquisition element) 102 and outputs the input image signals that have been converted to digital image signals to the image-capturing-mode selecting portion 104.

The image-capturing-mode selecting portion 104 possesses a plurality of image-capturing modes in advance and, from these, selects an image-capturing mode input by a user via the external I/F portion 113. Furthermore, the image-capturing-mode selecting portion 104 applies image processing to the input image signals acquired from the A/D converter 103 in accordance with the selected image-capturing mode and outputs the processed signals to the signal-value-region setting portion 106 and the buffer 105. For example, in addition to a normal mode, the image-capturing modes include modes such as a firework mode and a night-view mode that are suitable for capturing subjects with a large brightness difference.

The buffer 105 temporarily stores the image signals to which the image processing in accordance with the image-capturing mode has been applied and information about the image-capturing mode and outputs the processed image signals and the information to the noise-level calculating portion 109 and the noise-reduction processing portion 110.

With regard to specific image-capturing modes, the signal-value-region setting portion 106 possesses information in which the image-capturing modes are associated with thresholds for setting a signal-value region, and, only when an image-capturing mode selected by the image-capturing-mode selecting portion 104 corresponds to a specific image-capturing mode, the signal-value-region setting portion 106 extracts a threshold corresponding to the image-capturing mode, sets a signal-value region at or below the threshold as a predetermined signal-value region, and outputs this information to the applied-noise-model setting portion 108. Accordingly, when the image-capturing mode selected by the image-capturing-mode selecting portion 104 does not correspond to a pre-registered specific image-capturing mode, the information about the predetermined signal-value region is not output to the applied-noise-model setting portion 108 from the signal-value-region setting portion 106.

Figure 3:
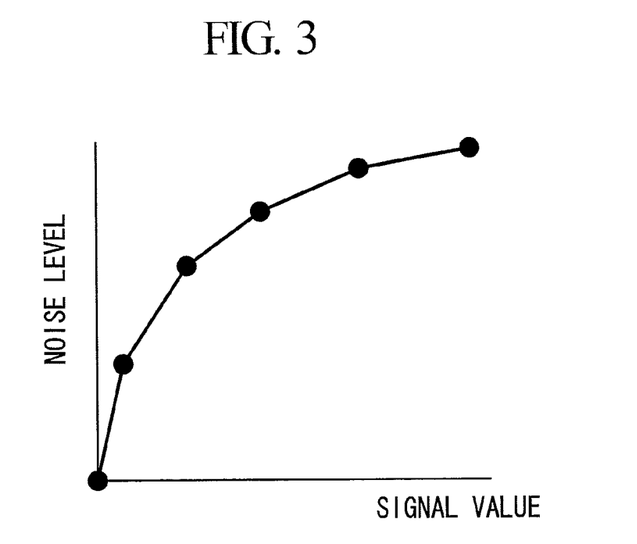
FIG. 3 is a diagram of the reference noise model represented by discrete points.

The reference-noise-model storing portion 107 stores a plurality of reference noise models determined by the properties of the CCD 102. Specifically, a reference noise model stores a reference noise model corresponding to the type and image-capturing mode of the CCD 102. FIG. 3 shows an example of the reference noise model. In FIG. 3, the horizontal axis is signal value and the vertical axis is noise level, and FIG. 3 shows that the noise level increases with an increase in the signal value.

Of the plurality of reference noise models stored in the reference-noise-model storing portion 107, the reference-noise-model selecting portion 114 selects a reference noise model that corresponds to the CCD 102 and the image-capturing mode used when the input image signals are acquired. The reference noise model selected by the reference-noise-model selecting portion 114 is output to the applied-noise-model setting portion 108.

In the case in which the predetermined signal-value region is input by the signal-value-region setting portion 106, the applied-noise-model setting portion 108 changes the noise model for the predetermined signal-value region in the reference noise model that has been input from the reference-noise-model selecting portion 114, and sets this as an applied noise model. Accordingly, it becomes possible to set an applied noise model in which the noise model for the predetermined signal-value region is different from the noise model for a signal-value region other than the predetermined signal-value region. At this time, the applied-noise-model setting portion 108 also sets the applied noise model so that noise levels at boundary between the predetermined signal-value region and the signal-value region other than the predetermined signal-value region are matched.

Accordingly, among the input image signals, a difference can be created in noise reduction between the predetermined signal-value region, such as a dark part, and the signal-value region other than the predetermined signal-value region. On the other hand, in the case in which the information about the predetermined signal-value region is not input by the signal-value-region setting portion 106, the applied-noise-model setting portion 108 outputs a reference noise model that has been input from the reference-noise-model selecting portion 114 to the noise-level calculating portion 109 without modification.

The applied-noise-model setting portion 108 will be described below in detail, using FIG. 2.

Figure 2:
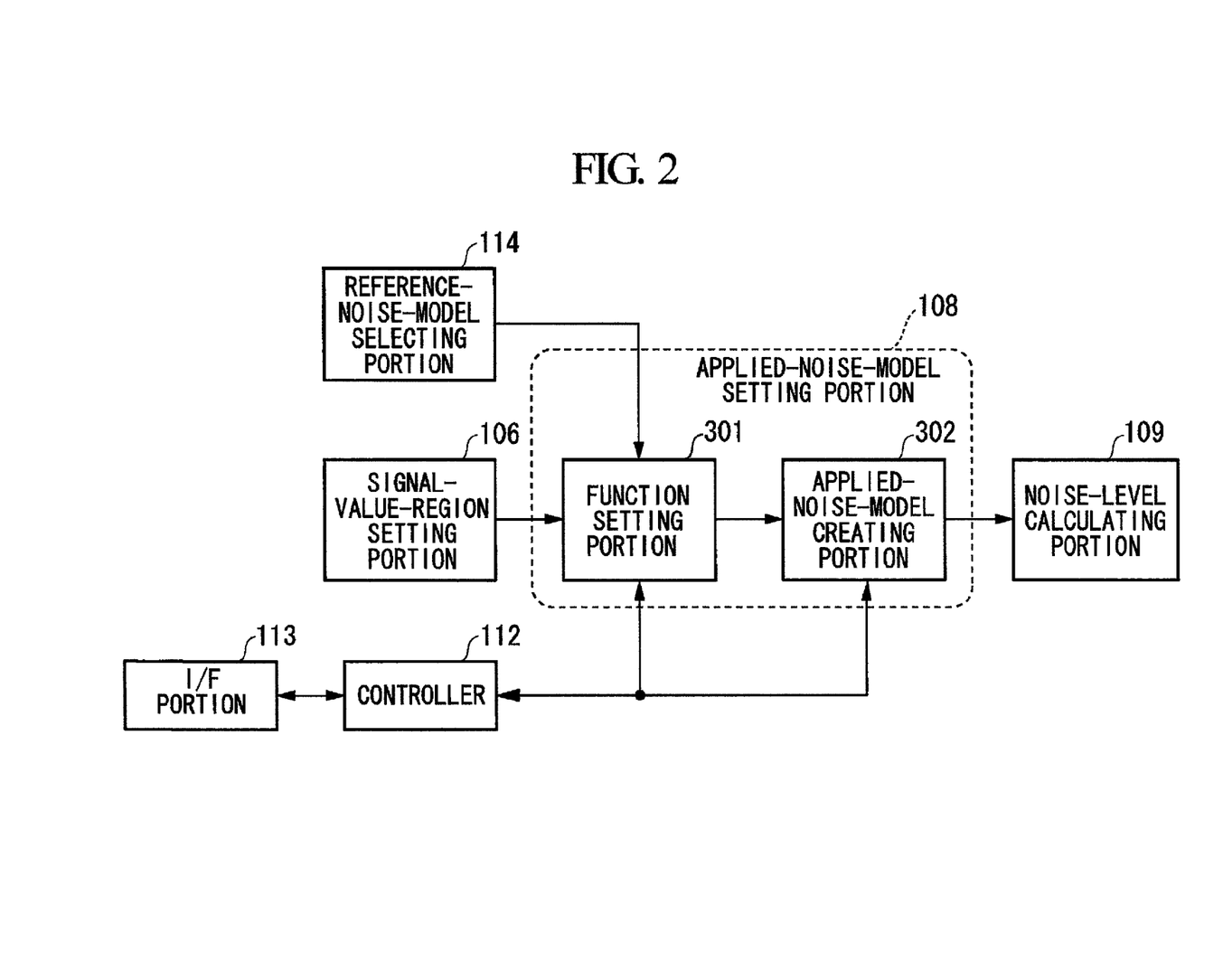
FIG. 2 is a diagram showing, in outline, the configuration of an applied-noise-model setting portion for the case in which a reference noise model shown in FIG. 1 is represented by a function.

As shown in FIG. 2, the applied-noise-model setting portion 108 is formed of a function setting portion 301 and an applied-noise-model creating portion 302.

The function setting portion 301 sets a function for transforming the noise model for the predetermined signal-value region in the reference noise model acquired from the reference-noise-model selecting portion 114. This function is given by the following Expression (1).

$$f(x)' = \alpha \cdot f(x) + \beta \quad (1)$$

Figure 5:
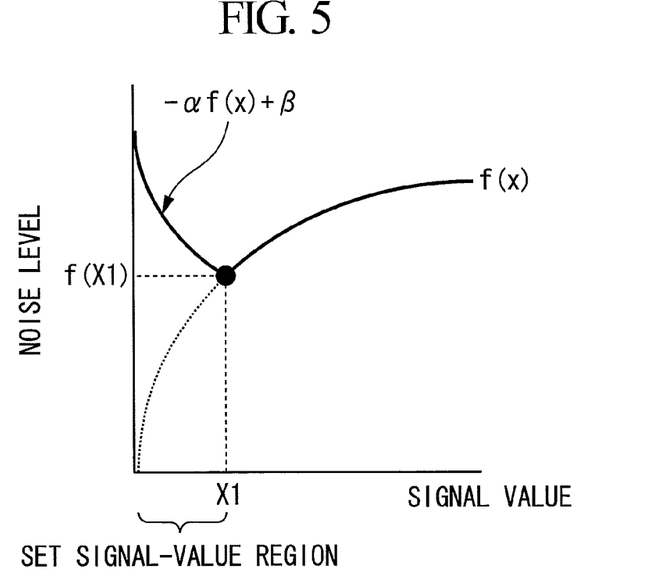
FIG. 5 is a diagram showing an example of an applied noise model for the case in which the reference noise model is represented by a function.

In the above-described Expression (1), $f(x)'$ is a noise model after the transformation, $f(x)$ is a reference noise model before the transformation, $\alpha$ is a negative coefficient, and $\beta$ is a positive coefficient. In addition, the above-described Expression (1) is, for example, represented as shown in FIG. 5.

The above-described Expression (1) is a function in which a reference noise model acquired from the reference-noise-model selecting portion 114 is multiplied by the negative coefficient $\alpha$, and the positive value $\beta$ is added thereto. The negative coefficient $\alpha$ and the positive value $\beta$ may be such that the user can set them through the external I/F portion 113 or may be predefined in accordance with the image image-capturing mode.

The applied-noise-model creating portion 302 uses the function expressed by the above-described Expression (1) set by the function setting portion 301 to transform the noise model for the predetermined signal-value region in the reference noise model, and thereby creates an applied noise model. Accordingly, the applied noise model becomes a noise model in which the noise model for the predetermined signal-value region is expressed as the above-described function and in which the reference noise model is employed, without modification, as the noise model for the signal-value region other than the predetermined signal-value region. At this time, the applied-noise-model creating portion 302 creates the applied noise model so that noise levels at boundary between the predetermined signal-value region and the signal-value region other than the predetermined signal-value region are matched.

The applied noise model created in this way is output to the noise-level calculating portion 109. Note that, as described above, in the case in which the information about the predetermined signal-value region is not input by the signal-value-region setting portion 106, that is, when an image-capturing mode does not correspond to a preregistered specific image-capturing mode, the applied-noise-model setting portion 108 outputs the reference noise model that has been input from the reference-noise-model selecting portion 114 to the noise-level calculating portion 109 without performing the above-described setting processing for the applied noise model.

The noise-level calculating portion 109 calculates a noise level for each signal value on the basis of the applied noise model set by the applied-noise-model setting portion 108, and outputs it to the noise-reduction processing portion 110.

The noise-reduction processing portion 110 reads out the input image signals stored in the buffer 105 and applies noise-reduction processing to the input image signals on the basis of the noise levels calculated by the noise-level calculating portion 109. Image signals to which the noise-reduction processing has been applied are output to the output portion 111.

The output portion 111 stores and saves the image signals to which the noise-reduction processing has been applied by the noise-reduction processing portion 110 in a storage medium such as a memory card or the like.

Next, the operation of an image processing system having the above-described configuration will be described.

Once image-capturing is performed by the user after image-capturing conditions, such as image-acquisition size, etc. are set via the external I/F portion 113, optical information about a subject is converted to analog image signals by the lens system 101 and the CCD 102, and the signals are input to the A/D converter 103. The input image signals, which are analog signals input to the A/D converter 103, are converted to digital image signals and the converted input image signals are output to the image-capturing-mode selecting portion 104. At the image-capturing-mode selecting portion 104, the image-capturing mode at the time of acquiring the input image signals is determined, and image processing in accordance with the this image-capturing mode is applied to the input image signals. The input image signals after the image processing are output to the buffer 105, the signal-value-region setting portion 106, and the reference-noise-model selecting portion 114 along with the information about the image-capturing mode.

At the buffer 105, the information about the image-capturing mode and the input image signals are temporarily stored and are then output to the noise-level calculating portion 109 and the noise-reduction processing portion 110. At the signal-value-region setting portion 106, in the case in which the image-capturing mode selected by the image-capturing-mode selecting portion 104 is the specific image-capturing mode, a predetermined signal-value region that corresponds to this image-capturing mode is selected and output to the applied-noise-model setting portion 108. At the reference-noise-model selecting portion 114, a reference noise model corresponding to the CCD 102 is extracted from the reference-noise-model storing portion 107 and output to the applied-noise-model setting portion 108.

At the applied-noise-model setting portion 108, in the case in which the information about the predetermined signal-value region is input by the signal-value-region setting portion 106, in the reference noise model input from the reference-noise-model selecting portion 114, the noise model for the predetermined signal-value region is transformed with the function expressed as the above-described Expression (1), thereby creating an applied noise model, and this applied noise model is output to the noise-level calculating portion 109. On the other hand, in the case in which the information about the predetermined signal-value region is not input from the signal-value-region setting portion 106, the applied-noise-model creating processing is not performed by the applied-noise-model setting portion 108, and the reference noise model input from the reference-noise-model selecting portion 114 is output to the noise-level calculating portion 109 without modification.

At the noise-level calculating portion 109, noise levels are calculated on the basis of the applied noise model set by the applied-noise-model setting portion 108, and the calculated noise levels are output to the noise-reduction processing portion 110. At the noise-reduction processing portion 110, noise-reduction processing is applied to the input image signals, which have temporarily been stored in the buffer 105, on the basis of the noise levels calculated by the noise-level calculating portion 109, and the image signals to which the noise-reduction processing has been applied are output to the output portion 111. At the output portion 111, the image signals to which the noise-reduction processing has been applied are stored and saved in a storage medium such as a memory card, or the like.

Note that, in the above-described embodiment, an image acquisition system that is integrated with the image acquisition apparatus provided with the lens system 101 and the CCD 102 has been described; however, the system need not be limited to such a configuration, and the image acquisition apparatus may be separately provided.

In other words, image signals acquired by a separate image-acquisition apparatus and stored in a storage medium, such as a memory card, or the like, in the form of unprocessed raw data may be read out from the storage medium and processed by an image processing apparatus.

In this case, however, information about image capturing (ISO speed, white balance factor, etc.) should be stored in a header portion, etc. Note that, transmission of various information from the separate image-acquisition apparatus to the image-signal processing apparatus is not limited to transmission via the storage medium, and it may be performed via a communication circuit, etc.

Furthermore, in this embodiment, image-signal processing is assumed to be performed by hardware; however, it need not be limited to such a configuration. For example, signals from the CCD 102 may be stored in a computer-readable storage medium, such as a memory card, or the like, as unprocessed raw data, and the information about image-capturing (ISO speed, white balance factor, etc.) from the controller 112 may also be stored in the storage medium as header information. Then, by causing a computer to execute an image-signal processing program, which is separate software, the information in the storage medium can be read out and processed by the computer.

In addition, transmission of various information from the image-acquisition apparatus to the computer is not limited to the transmission via the storage medium, as with the case described above, and the transmission may be performed via a communication circuit, etc.

Figure 9:
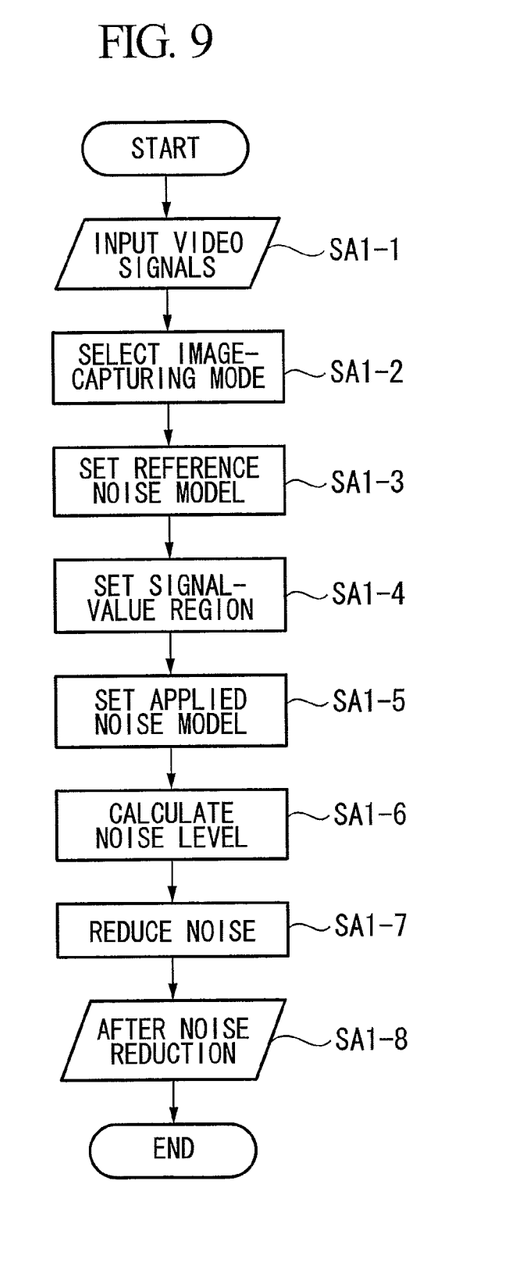
FIG. 9 is a diagram showing the operation flow of processing according to the first and second embodiments of the present invention.

The processing procedure of an image processing method realized by causing the computer to execute an image-processing program will be described with reference to FIG. 9. FIG. 9 is a diagram showing the operation flow with regard to the image-signal processing realized by the above-described image processing apparatus.

First, when input image signals and header information are input (Step SA 1-1), an image-capturing mode is selected on the basis of this header information (Step SA 1-2). Subsequently, a reference noise model corresponding to the image-capturing mode selected in Step SA 1-2 is set (Step SA 1-3), and, furthermore, a signal-value region is set (Step SA 1-4). Next, an applied noise model is set by using the reference noise model selected in Step SA 1-3 and the predetermined signal-value region set in Step SA 1-4 (Step SA 1-5); noise levels of the input image signals are calculated by using the applied noise model (Step SA 1-6); and noise-reduction processing is performed on the basis of the calculated noise level (Step SA 1-7). The noise-reduced image signals that have been processed in Step SA 1-7 are output, and this processing is completed (Step SA 1-8).

Figure 10:
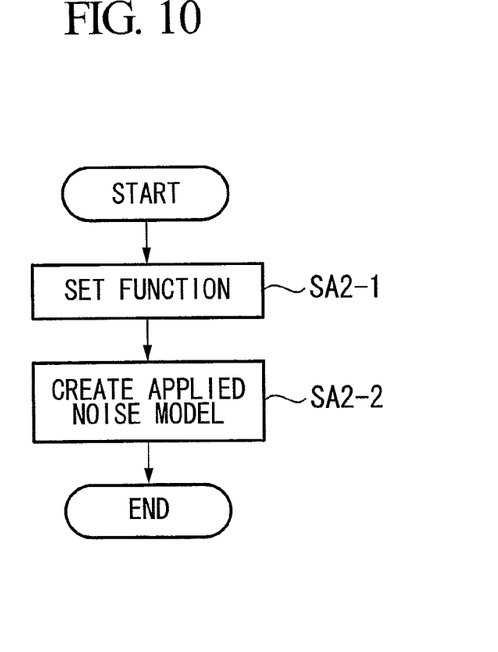
FIG. 10 is a diagram showing the operation flow of applied-noise-model setting processing.

FIG. 10 shows the operation flow with regard to the applied-noise-model setting processing in the above-described Steps SA 1-5. First, a function for transforming the reference noise model is set (Step SA 2-1). Next, an applied noise model is created by using the function set in Step SA 2-1 (Step SA 2-2).

As has been described, with the image-processing apparatus, method, and program according to this embodiment, because the noise model for the predetermined signal-value region and the noise model for a signal-value region other than the predetermined signal-value region are different, it becomes possible to create a difference in noise reduction between the predetermined signal-value region and the signal-value region other than the predetermined signal-value region. Accordingly, noise-reduction processing can be more reliably applied to the predetermined signal-value region among the input image signals, such as a dark part, etc., in accordance with the image-capturing mode, and it becomes possible to perform optimal noise-reduction processing for the input image signals.

First Modification

In this embodiment, the function setting portion is configured to set a function such as one expressed as the above-described Expression (1); however, this function is not limited to this example. For example, a function in which the noise level in the predetermined signal-value region is set to be constant at f(i), as represented by Expression (2) below, may be set.

$$f(x)' = f(i) \qquad (2)$$

Figure 4:
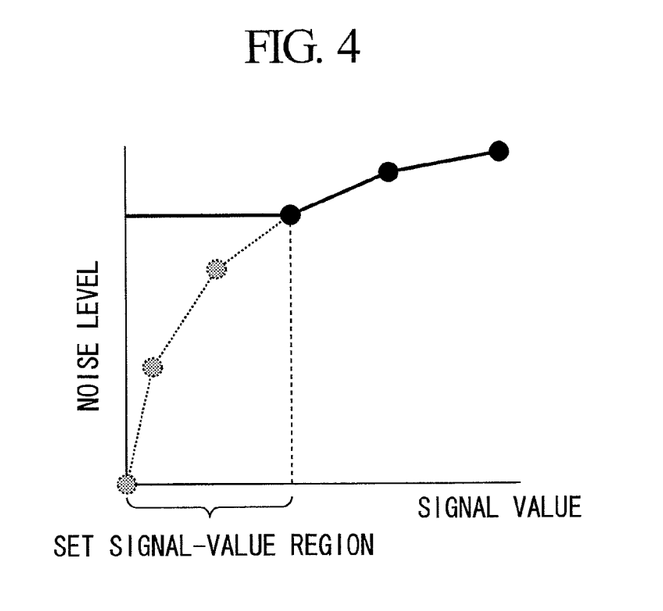
FIG. 4 is a diagram showing an example of an applied noise model for the case in which the reference noise model is represented by discrete points.

Note that, the above-described Expression (2) is represented, for example, as shown in FIG. 4. In addition, in the above-described Expression (2), f(x)' is a converted noise model, f(i) is a noise level of a reference noise model at boundary i between a predetermined signal-value region and signal-value region other than the predetermined signal-value region.

Second Modification

Figure 6:
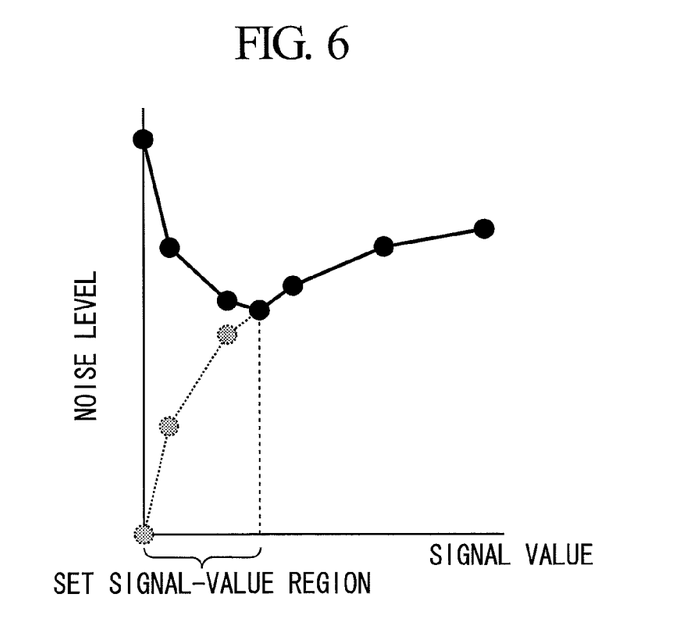
FIG. 6 is a diagram showing an example of an applied noise model for the case in which the reference noise model is represented by discrete points.

In addition, in this embodiment described above, the reference noise model is assumed to be continuous values expressed by a function; however, it is not limited to this example. For example, a reference noise model may be expressed by a plurality of discrete signal values, information about noise levels for these signal values, and information about the inclination of a straight line that connects the noise levels. Such a reference noise model is expressed, for example, as shown in FIG. 6. In this case, the applied-noise-model setting portion 108 creates a reference noise model that is expressed as continuous values from these values, and creates an applied noise model by using this model.

Third Modification

Figure 7:
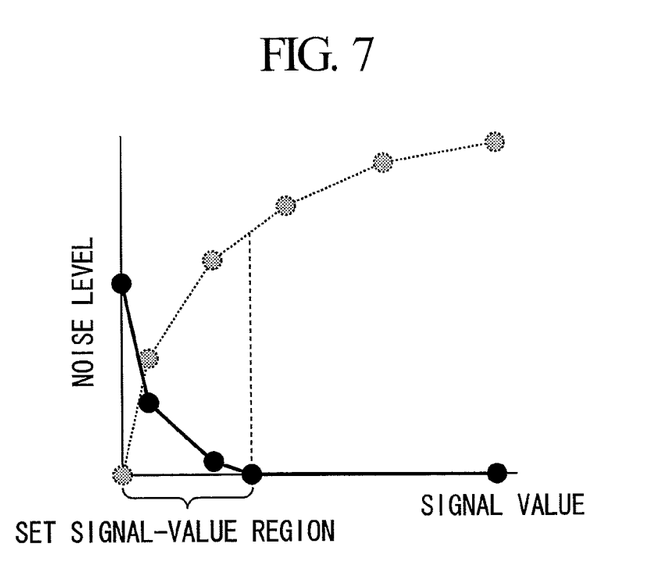
FIG. 7 is a diagram showing an example of an applied noise model for the case in which the reference noise model is represented by discrete points.

In this embodiment, for the signal-value region other than the predetermined signal-value region in the applied noise model, the reference noise model is not subjected to processing, and the reference noise model is set without modification; however, it is not limited to this example. For example, the noise level may be set as 0 for the signal-value region other than the predetermined signal-value region. Such an example is shown in FIG. 7.

Note that, in this embodiment, a case in which the image processing apparatus of the present invention is applied to a digital camera has been described as an example; however, it is not limited thereto, and applications for other image-acquisition systems assumed for video image are also possible.

In addition, in this embodiment, with regard to the method of setting the signal-value region, the setting is performed on the basis of the thresholds stored in advance for specific image-capturing modes; however, it is not limited thereto, and a threshold for setting a signal-value region in which noise reduction needs to be increased may be manually set by a user through the external I/F portion 113.

Additionally, in this embodiment, for setting the applied noise reduction model, in the case of a specific image-capturing mode, an applied noise model is set by performing conversion processing of the noise level by using a function on the basis of the reference noise model; however, it is not limited thereto, and the setting may be performed by preregistering applied noise models in which noise models differ between the predetermined signal-value region and the signal-value region other than the predetermined signal-value region and by extracting a predefined applied noise model corresponding to an image-capturing mode.

Second Embodiment

Next, an image-processing apparatus according to a second embodiment of the present invention will be described with reference to the drawings.

In this embodiment, a case in which the image processing apparatus of the present invention is applied to an endoscope apparatus will be described. In the following descriptions of the image processing apparatus according to this embodiment, descriptions of components in common with those in the first embodiment will be omitted and differences will be mainly described.

FIG. 1 is a block diagram showing an example configuration of the image acquisition system according to the second embodiment of the present invention. As shown in FIG. 1, in the image processing apparatus according to this embodiment, although components provided in the above-described first embodiment are the same, the lens system 101 and the CCD 102 in FIG. 1 are included in an endoscope scope.

In an endoscope apparatus, image-capturing modes include a normal image-capturing mode, in which image-capturing observation is performed with normal light, and a special image-capturing mode, in which image-capturing observation is performed with special light. For example, an example of the special image-capturing mode is known narrow-band imaging (NBI).

In addition, the reference-noise-model storing portion 107 stores a plurality of reference noise models corresponding to the above-described image-capturing modes and each endoscope scope. At this time, in the case in which gain is automatically changed in accordance with illumination intensities, reference noise models for each gain may be additionally stored.

Figure 8:
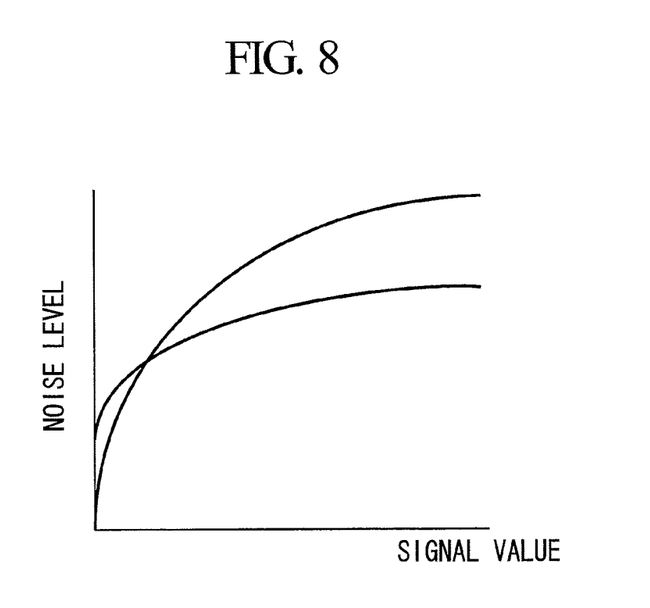
FIG. 8 is a diagram showing an example of a case in which there are a plurality of reference noise models represented by functions.

FIG. 8 shows an example of the reference noise model. In FIG. 8, the horizontal axis is the signal value and the vertical axis is the noise level, and the model has a characteristic that the noise level increases with increasing signal value. This characteristic differs depending on the type and gain of the image-capturing mode and the endoscope scope.

In addition, in this embodiment, from the plurality of reference noise models, the reference-noise-model selecting portion 114 selects a reference noise model that corresponds to the image-capturing mode, the installed endoscope scope, and the gain.

As has been described, with the image processing apparatus, method, and program according to this embodiment, because a noise model for a predetermined signal-value region and a noise model for a signal-value region other than the predetermined signal-value region are different, it becomes possible to create a difference in noise reduction between the predetermined signal-value region and the signal-value region other than the predetermined signal-value region. Accordingly, for example, in a case such as observing a blood vessel at a high contrast by using the narrow band imaging (NBI), a difference can be created in noise reduction between noise reduction for blood and a mucosal surface layer, and it becomes possible to improve the precision of observing a diseased portion.

Furthermore, in the case in which the gain is automatically changed in accordance with the illumination intensity in an input image, by selecting a reference noise model in accordance with the gain, it becomes possible to perform noise reduction in accordance with the illumination intensity. Accordingly, for example, in the case where the narrow band imaging (NBI) is employed, it becomes possible to improve the precision of observing a diseased portion.

Note that the image acquisition system according to this embodiment may be, as in the case of the above-described first embodiment, an image acquisition system in which the image acquisition apparatus is separately provided. In addition, similar processing may be performed by causing a computer to execute an image-signal processing program.

Note that, in the above descriptions, digital cameras and endoscope apparatuses are described as examples of image acquisition systems; however, without limitation to these, the image processing apparatus, method, and program of the present invention can be applied to a wide variety of systems that process image signals. For example, the present invention can be applied to video digital cameras that handle video images.

REFERENCE SIGNS LIST 104 image-capturing-mode selecting portion
106 signal-value-region setting portion
107 reference-noise-model storing portion
108 reference-noise-model setting portion
109 noise-level calculating portion
110 noise-reduction processing portion
114 reference-noise-model selecting portion
301 function setting portion
302 applied-noise-model creating portion

The invention claimed is:

1. An image processing apparatus comprising:
    an image-capturing-mode selecting portion configured to select one image-capturing mode from a plurality of image-capturing modes;
    a signal-value-region setting portion configured to set a predetermined signal-value region on image signals input from an image-acquisition element;
    a noise-level calculating portion configured to calculate noise levels;
    a noise-reduction processing portion configured to perform noise reduction processing on the input image signals based on the noise levels calculated by the noise-level calculating portion; and
    a reference-noise-model storing portion configured to store a plurality of reference noise models determined in accordance with properties of the image-acquisition element;
    wherein:
    each reference noise model indicates a relationship between signal value and noise level, and has a characteristic such that the noise level increases with an increase in the signal value;
    the signal-value-region setting portion is configured to set a signal-value region as the predetermined signal-value region, signal values of the signal-value region being at or below a threshold from among a plurality of thresholds determined in association with the image-capturing modes, when the image-capturing mode selected by the image-capturing-mode selecting portion is a specific image-capturing mode;
    the noise-level calculating portion is configured to calculate (i) a noise level of a signal-value region other than the predetermined signal-value region, based on a reference noise model, and (ii) a noise level of the predetermined signal-value region, based on an applied noise model, the applied noise model being modified so that the noise level of the predetermined signal-value region is higher than the noise level of the reference noise model which corresponds to the image-capturing mode selected by the image-capturing-mode selecting portion, when the predetermined signal-value region is set by the signal-value-region setting portion; and the noise-level calculating portion is configured to calculate a noise level of an entire region of the input image signals based on the reference noise model, when the predetermined signal-value region is not set by the signal-value-region setting portion.

2. A non-transitory computer-readable recording medium having recorded thereon an image processing program which is executable to control a computer to perform functions comprising:

image-capturing-mode selecting processing for selecting one image-capturing mode from a plurality of image-capturing modes;

signal-value-region setting processing for setting a predetermined signal-value region on image signals input from an image-acquisition element;

noise-level calculating processing for calculating noise levels;

noise-reduction processing for performing noise reduction processing on input image signals based on the calculated noise levels; and reference-noise-model storing processing for storing a plurality of reference noise models determined in accordance with properties of the image-acquisition element;

wherein:

each reference noise model indicates a relationship between signal value and noise level, and has a characteristic such that the noise level increases with an increase in the signal value;

the signal-value-region setting processing sets a signal-value region as the predetermined signal-value region, signal values of the signal-value region being at or below a threshold from among a plurality of thresholds determined in association with the image-capturing modes, when the image-capturing mode selected by the image-capturing-mode selecting processing is a specific image-capturing mode;

the noise-level calculating processing calculates (i) a noise level of a signal-value region other than the predetermined signal-value region, based on a reference noise model, and (ii) a noise level of the predetermined signal-value region, based on an applied noise model, the applied noise model being modified so that the noise level of the predetermined signal-value region is higher than the noise level of the reference noise model which corresponds to the image-capturing mode selected by the image-capturing-mode selecting processing, when the predetermined signal-value region is set by the signal-value-region setting processing; and the noise-level calculating processing calculates a noise level of an entire region of the input image signals based on the reference noise model, when the predetermined signal-value region is not set by the signal-value-region setting processing.

3. An image processing method comprising:

selecting one image-capturing mode from a plurality of image-capturing modes;

setting a predetermined signal-value region on image signals input from an image-acquisition element;

calculating noise levels;

performing noise reduction processing on input image signals based on the calculated noise levels; and storing a plurality of reference noise models determined in accordance with properties of the image-acquisition element;

wherein:

each reference noise model indicates a relationship between signal value and noise level, and has a characteristic such that the noise level increases with an increase in the signal value;

the setting the predetermined signal-value region comprises setting a signal-value region as the predetermined signal-value region, signal values of the signal-value region being at or below a threshold from among a plurality of thresholds determined in association with the image-capturing modes, when the image-capturing mode selected by the selecting is a specific image-capturing mode;

the calculating the noise levels comprises calculating (i) a noise level of a signal-value region other than the predetermined signal-value region, based on a reference noise model, and (ii) a noise level of the predetermined signal-value region, based on an applied noise model, the applied noise model being modified so that the noise level of the predetermined signal-value region is higher than the noise level of the reference noise model which corresponds to the image-capturing mode selected by the selecting, when the predetermined signal-value region is set by the setting; and the calculating the noise levels comprises calculating a noise level of an entire region of the input image signals based on the reference noise model, when the predetermined signal-value region is not set by the setting.

* * * * *